United States Patent [19]

Sysko

[11] 4,360,463

[45] Nov. 23, 1982

[54] PURE 6,6-DIIODOPENICILLANIC ACID AND PROCESS FOR ITS PREPARATION

[75] Inventor: Robert J. Sysko, Niantic, Conn.

[73] Assignee: Pfizer Inc., New York, N.Y.

[21] Appl. No.: 298,678

[22] Filed: Sep. 2, 1981

[51] Int. Cl.³ .................................... C07D 499/04
[52] U.S. Cl. ......................... 260/245.2 R; 424/270; 424/271; 260/239.1
[58] Field of Search .............. 260/239.1, 245.2 R; 424/270

[56] References Cited

FOREIGN PATENT DOCUMENTS 2045755 11/1980 United Kingdom .
2051046 1/1981 United Kingdom .

OTHER PUBLICATIONS

Clayton, J. Chem. Soc., Part C, 2123 (1969).
CA, vol. 94, 121511(s) 1981.
CA, vol. 94, 84113(r) 1981.

Primary Examiner—Nicholas S. Rizzo
Attorney, Agent, or Firm—Charles J. Knuth; Albert E. Frost; Peter C. Richardson

[57] ABSTRACT

An improved process for making 6,6-diiodopenicillanic acid, an intermediate for preparation of 6-beta-iodopenicillanic acid, a beta-lactamase inhibitor, which comprises diazotizing 6-beta-aminopenicillanic acid in the presence of iodine, followed by washing the product of said process with an aqueous solution of an alkali metal iodide.

4 Claims, No Drawings

4,360,463

PURE 6,6-DIIODOPENICILLANIC ACID AND PROCESS FOR ITS PREPARATION

BACKGROUND OF THE INVENTION

The best known and most widely used class of antibacterial agents is the beta-lactam antibiotics. However, said beta-lactam antibiotics, comprising penicillins and cephalosporins, despite their wide use would find even greater use except for the fact that certain penicillins and cephalosporins are not active against microorganisms which produce a beta-lactamase; i.e., an enzyme which cleaves the beta-lactam ring of penicillins and cephalosporins to products devoid of antibacterial activity.

Certain substances, known as beta-lactamase inhibitors, have the ability to inhibit beta-lactamases and, when used in combination with a penicillin or cephalosporin enhance the antibacterial effectiveness of said penicillin or cephalosporin against beta-lactamase producing microorganisms.

The present invention relates to an improved process for making 6,6-diiodopenicillanic acid. More specifically it relates to a process for making pure 6,6-diiodopenicillanic acid which comprises diazotizing 6-beta-aminopenicillanic acid in the presence of iodide, followed by washing the product of said process with an aqueous solution of an alkali metal iodide. It also relates to pure 6,6-diiodopenicillanic acid.

Clayton, J. Chem. Soc., Part C, 2123 (1969) reported that diazotization of 6-beta-aminopenicillanic acid in the presence of sodium iodide gave a crude product consisting of 55% of 6,6-diiodopenicillanic acid and 45% 6-alpha-iodopenicillanic acid.

British Patent Application 2,051,046A, published Jan. 14, 1981, describes the preparation of 6,6-diiodopenicillanic acid, and its morphine salt, by diazotization of 6-beta-aminopenicillanic acid in the presence of iodine. Unreacted iodine was removed by washing the product with aqueous sodium thiosulfate and the resulting product converted to its morpholine salt in about 60% yield. Conversion of the thus-produced 6,6-diiodopenicillanic acid morpholine salt to 6,6-diiodopenicillanic acid dimethylsulfoxide solvate is also reported.

The preparation of pure 6,6-diiodopenicillanic acid per se is not reported in the literature.

The preparation of 6,6-dibromopenicillanic acid by diazotization of 6-beta-aminopenicillanic acid in the presence of bromine followed by removal of unreacted and/or excess bromine from the reaction product of said process is reported in British Patent Application 2,045,755A, published Nov. 5, 1980.

Attempts to prepare 6,6-diiodopenicillanic acid by analogy to the process of British Application 2,045,755A substituting, of course, iodine for bromine, produced, at best, poor yields of 6,6-diiodopenicillanic acid. Failure to conduct the bisulfite treatment in the least time possible gave only degradation products.

SUMMARY OF THE INVENTION

It has now been unexpectedly and surprisingly found that pure 6,6-diiodopenicillanic acid can be prepared in good yield by diazotization of 6-beta-aminopenicillanic acid in the presence of iodine, followed by removal of elemental iodine from the product of said process by washing it with an aqueous solution of an alkali metal iodide.

DETAILED DESCRIPTION OF THE INVENTION

The process of this invention comprises diazotizing 6-beta-aminopenicillanic acid (6-APA) in a reaction-inert solvent such as ethyl acetate, methylene chloride, toluene, diethyl ether, diisopropyl ether, and toluene at a temperature from about 0° C. to about 10° C. by reaction with sulfuric acid and sodium nitrite in the presence of iodine. The sodium nitrite can be used in solid form or as an aqueous solution. Molar ratios of 6-APA:-$NaNO_2$:$I_2$ of from about 1:2:1 to about 1:2:3 are generally used. Higher ratios of iodine can be used but afford no advantage. For optimum yield of desired product the above stated proportions are especially effective.

The iodine can be added in solid form or in solution in a suitable solvent such as ethyl acetate, diethyl ether or methylene chloride, or other reaction-inert solvent.

The reaction product of said diazotization in the presence of iodine is recovered from the reaction mixture by separation of the organic phase followed by evaporation thereof. The solid, usually tan to red-brown in color, residue remaining is then washed, generally by slurrying, with an aqueous solution of an alkali metal iodide, such as sodium or potassium iodide. This step successfully removes unreacted and/or excess iodine without degradation of the desired 6,6-diiodopenicillanic acid.

Sufficient aqueous alkali metal iodide solution is used to completely remove all iodine from the reaction product, as evidenced by removal of all color from said reaction product. The concentration of the aqueous alkali metal iodide solution is not critical. Concentrations ranging from 5% to 25% (w/v) are very effective in removing the iodine. Higher or lower concentrations can be used if desired. However, higher concentrations may require additional washing of the de-iodinated product. Lower concentrations, particularly for large scale operation require the handling of unnecessarily large volumes of liquid.

The aqueous alkali metal iodide wash is generally carried out at ambient temperature for the sake of convenience. However, temperature is not critical and this step can be conducted at any temperature from about 0° C. to 100° C. Temperatures at either extreme of this range are usually avoided for reasons of convenience and economy.

In contrast to the 6,6-diiodopenicillanic acid produced by Clayton (loc. cit.), the 6,6-diiodopenicillanic acid produced by the process of this invention is free of 6-monoiodopenicillanic acids. Additionally, the present process affords improved yields of said 6,6-diiodo compound over those reported in the literature.

6,6-Diiodopenicillanic acid is converted to 6-beta-iodopenicillanic acid, a beta-lactamase inhibitor, by reduction with an organotin monohydride such as tri-(n-butyl)tin hydride at temperatures from 0° to 110° C. as is described in Belgian Pat. No. 882,027, granted Sept. 3, 1980.

EXAMPLE 1

6,6-Diiodopenicillanic Acid

To a solution of iodine (105.6 g., 416 mmoles) in ethyl acetate (285 ml.) at 0° C. was added 2.5 N $H_2SO_4$ (124.5 ml.) over a period of ten minutes. Sodium nitrite (19.17 g., 279 mmoles) was then added over a twenty minute period while maintaining the temperature at 0° C. 6-

Beta-aminopenicillanic acid (30.0 g., 138.1 mmoles) was added to the reaction mixture over a 30 minute period at 0°–5° C. The resulting mixture was stirred for fifteen minutes at 0° C., ethyl acetate (285 ml.) at 0° C. added and the mixture filtered through diatomaceous earth. The ethyl acetate layer was separated from the filtrate, dried over magnesium sulfate, and then evaporated in vacuo. The solid residue remaining was slurried for twenty minutes at room temperature in 10% aqueous sodium iodide solution (500 ml.) and the solid recovered by filtration. The solid was slurried in water (500 ml.), the slurry filtered and the sodium iodide and water washes repeated. The solid product was dried in vacuo at room temperature. Yield=44.5 g. (71%); m.p. 128°–132° C.

NMR: $\delta_{CDCl_3}^{TMS}$: 9.65 (s, 1-COOH), 5.72 (s, 1-C$_5$-H), 4.45 (s, 1-C$_6$-H), 1.70 and 1.55 (s, 6-CH$_3$'s).

EXAMPLE 2

Repetition of the above procedure but using 279 mmoles (70.4 g.) of I$_2$ affords substantially the same results as realized in Example 1.

I claim:

1. In the process for making 6,6-diiodopenicillanic acid by the diazotization of 6-beta-aminopenicillanic acid in the presence of iodine, the improvement which comprises washing the product of said process with an aqueous alkali metal iodide solution.

2. The process of claim 1 wherein said alkali metal iodide is sodium iodide.

3. The process of claim 1 wherein said alkali metal iodide is potassium iodide.

4. Pure 6,6-diiodopenicillanic acid.

* * * * *